US006720013B2

(12) United States Patent
Johnson et al.

(10) Patent No.: US 6,720,013 B2
(45) Date of Patent: Apr. 13, 2004

(54) INSECT REPELLANT-CONTAINING MINERAL SUPPLEMENT

(75) Inventors: Louis B. Johnson, Troy, AL (US); William Whitehead, Troy, AL (US)

(73) Assignee: B & L Technologies, Troy, AL (US)

( * ) Notice: Subject to any disclaimer, the term of this patent is extended or adjusted under 35 U.S.C. 154(b) by 0 days.

(21) Appl. No.: 10/114,070

(22) Filed: Apr. 3, 2002

(65) Prior Publication Data

US 2003/0133996 A1 Jul. 17, 2003

Related U.S. Application Data

(60) Provisional application No. 60/347,889, filed on Jan. 15, 2002.

(51) Int. Cl.⁷ .................. A61K 33/04; A61K 35/78; A01N 65/00; A23K 1/16; A23K 1/175
(52) U.S. Cl. .................. 424/705; 424/680; 424/754; 424/637; 424/695; 424/696; 424/697; 424/699; 424/701; 424/703; 424/704; 424/706; 424/707; 424/708; 424/709; 424/710; 424/711; 424/712; 424/713; 424/714; 424/438; 424/439; 424/442; 424/DIG. 10; 514/706; 514/905; 514/919; 426/2; 426/648

(58) Field of Search .................. 424/754, 637, 424/695, 696, 697, 699, 701, 703–714, DIG. 10, 680, 438, 439, 442; 514/919, 706, 905; 426/2, 648

(56) References Cited

U.S. PATENT DOCUMENTS

| 3,794,740 | A | | 2/1974 | Achorn et al. ............ 426/69 |
| 4,197,319 | A | * | 4/1980 | Betz et al. ............... 426/2 |
| 4,540,577 | A | | 9/1985 | Hunt et al. ............... 424/679 |
| 4,861,585 | A | | 8/1989 | Galef, Jr. et al. ......... 424/84 |
| 5,268,357 | A | | 12/1993 | Yabiki et al. ............. 514/8 |
| 6,244,217 | B1 | | 6/2001 | Robbins ................... 119/174 |

* cited by examiner

*Primary Examiner*—John Pak
(74) *Attorney, Agent, or Firm*—Clark & Brody

(57) ABSTRACT

A mineral supplement or feed for ruminant animals, especially deer, contains effective amounts of sulfur and garlic to repel insects from the animals. By inducing the repellant into the animal via ingestion of the mineral supplement or feed, disease and stress in the animals as caused by the insects is reduced.

5 Claims, No Drawings

INSECT REPELLANT-CONTAINING MINERAL SUPPLEMENT

This application claims priority under 35 USC 119(e) from provisional patent application No. 60/347,889 filed on Jan. 15, 2002.

FIELD OF THE INVENTION

The present invention is directed to an improved ruminant animal mineral supplement and animal feed, and particularly one containing effective amounts of sulfur and garlic for insect repellency.

BACKGROUND ART

In the prior art, it is well know to provide mineral supplements to ruminant animals. One reason for this is that minerals are important in antler development, and an animal's diet does not always supply the necessary minerals for optimum antler growth.

As such, it is common for many hunters and landowners to establish mineral licks on their property, providing that such are permitted by law.

Besides antler growth, studies have shown that mineral supplementation increases forage uptake, improves forage digestion, and increases reproductive success.

An example of a mineral supplement is shown in U.S. Pat. No. 6,244,217 to Robbins, herein incorporated in its entirety by reference.

While mineral supplements provide significant improvements in the health of ruminant animals, insects continue to be a problem for animal health. Internal and external parasites have plagued deer and cattle for centuries. These pests reduce weight gain, and increase stress for the animals.

Accordingly, there is a need to provide improved insect repellants for use on ruminant animals.

The present invention solves this need by providing an insect repelling mineral supplement and/or feed that contains effective amounts of garlic and sulfur.

While it is know to use garlic powder as a feed additive for livestock, U.S. Pat. No. 5,268,357 to Yabiki et al., there is no suggestion of its use in mineral supplements for insect repellency. Yabiki et al. also do not teach the use of garlic and sulfur as part of a feed.

The Robbins patent discloses a mineral supplement that suggests that sulfur be present. However, Robbins does not exemplify a mineral supplement with sulfur, the nutrient lists do not show any sulfur. At most, the sulfur in the Robbins supplement would be in amounts to supply the needs of the animal's for health and nutrition, similar to an RDA in vitamins, e.g., generally a trace amount compared to the other main constituents of the supplement (a micro mineral as compared to a macro mineral). However, this patent does not identify amounts, nor suggest that the sulfur be in amounts for insect repellency.

Other feed supplements employ sulfur, see U.S. Pat. No. 3,794,740 to Achorn et al., but in the form of ammonium sulphate and levels of 0.33% by weight.

SUMMARY OF THE INVENTION

It is a first object of the present invention to provide an improved mineral supplement or animal feed for ruminant animals.

Another object of the invention is a mineral supplement or feed that provides insect repellency.

One other object of the invention is a method of repelling insects from ruminant animals by modifying a mineral supplement or animal feed through the addition of effective amounts of garlic and sulfur.

Other objects and advantages of the present invention will become apparent as a description thereof proceeds.

The invention entails improvements in mineral supplements, particularly mineral licks for deer. The improvement comprises having the mineral supplement contain an effective amount of garlic and sulfur for insect repellency. The mineral supplement mineral supplement can be either solid, liquid, or powder, and when in solid form, is preferably in the form of a mineral lick. It is preferred that the mineral supplement contains at least about 25% by weight of salt content, and more preferably a majority of salt.

The invention also entails a method of repelling insects for ruminant animals by adding an effective amount of garlic and sulfur to a ruminant animal mineral supplement; and placing the mineral supplement in one or more locations that are accessible by the ruminant animals. The mineral supplement as the solid, liquid, or granular and is preferably placed in the wild location such as a forest, or the like.

It is preferred that the garlic and sulfur amounts are at least 0.1% garlic and 0.5% sulfur on a weight basis of the supplement. The sulfur percentage is based on elemental sulfur, so that the amount of compounds containing other elements than sulfur may exceed the 0.5% elemental sulfur target. The garlic could range from at least 0.1% to up to 5%, more preferably up to 2.0% or 3.0%, and the sulfur could range from 0.5% to up to 10%, if desired. It should be understood that the upper limits of the sulfur and garlic relate more to the attractive and/or health effect of the mineral supplement, too much sulfur or garlic may actually repel deer from using the supplement. Too much sulfur may also be harmful to an animal.

Another aspect of the invention is the use of effective amounts of the garlic and sulfur in an animal feed for insect repellency. Typically, smaller or reduced amounts of the sulfur and garlic are used when made part of an animal feed since the animal's intake of the feed is generally much greater in weight percentage than that consumed when ingesting a supplement.

DESCRIPTION OF THE PREFERRED EMBODIMENTS

The present invention offers significant improvements in the treatment of ruminant animals.

It is believed that the use of garlic as a component of the mineral supplement or animal feed helps repel insects as the animals sweat the garlic that has been ingested. Garlic also helps the animal's heart while at the same time reducing cholesterol.

The presence of sulfur is also advantageous in that it has medicinal properties and repels insects and snakes. When ingested, the sulfur will repel insects when it is sweated out by the animals.

The amount of garlic and sulfur is deemed to be an effective amount to function in its intended role as an insect repellant when sweated out of an animal. The effective amount may vary depending on the animal, and its size. The amount should be sufficient so that the garlic and sulfur leave the animal via sweat for insect repellency. It is believed that at least 0.10% garlic of the supplement on a weight basis should be sufficient for most animals. A preferred range of garlic would be up to 5.0%. More preferred ranges for garlic on a weight basis would be 0.1–5.0%, with an even more preferred range of 0.5 to 2.0 or 3.0%, and a target of around 0.8 to 1.20% or around 1.0%.

Similarly, at least about 0.5% sulfur should be used, with a preferred target being about at least 1% and up to about 10%. More preferred ranges for sulfur on a weight basis would be 0.5–6.0%, with an even more preferred range of 2.0–4.0%, and a target of around 2.5 to 3.5%, or around 3.0%.

The garlic can be added to the supplement in any known form. The form of garlic may depend on the form of the mineral supplement. Typically, supplements come in liquid, granular, and solid form, and the form of garlic would be chosen depending on the form of the supplement. It is preferred to use garlic powder or granules since this is an economical form of garlic. However, garlic oil could also be employed. In fact, garlic substitutes could be used as well. Aquaresins and oleoresins could also be used as a garlic source.

Likewise, the form of sulfur would also be related to the form of the supplement. In addition, the sulfur could be added in its pure form, or as a compound, e.g., sulfates, sulfides, and the like. As with garlic, it is preferred to add sulfur powder due to its cost and ease in making the final mineral supplement product.

The inventive mineral supplement is distinguished from known feed supplements in that feed supplements supply all the nutrition that the animal requires. In contrast, mineral supplements are akin to the vitamins people take on daily basis. To supply all of the nutritional requirements, feeds often employ proteins, carbohydrates, fiber, molasses, or other components that are typically found in feeds. The aim of the supplement aspect of the invention is not to feed the ruminant animals but provide an insect repellant as part of a mineral supplement. In this mode of the invention, there is no need to employ a feed component, and in fact, the presence of such a component may attract undesirable animals and lessen the impact of the insect repellant on the target population of ruminant animals.

Another distinguishing characteristic of the inventive mineral supplement is the presence of salts. The salt amount is generally at least 25% on a weight basis, and these levels are not found in feeds. For example, some supplements have up to 95% salt with the balance being 5.0% of the remaining components. However, it is believed that about 25% or even a majority of salt is needed to overcome the taste of the minerals, which tend to be bitter. The salt used is that typically found in mineral supplements, e.g., sodium chloride, etc.

An exemplary supplement could be obtained by modifying a commercially available supplement such Persimmon Pit, which is distribute sold by Johnson Laboratories of Troy Ala. Typically, this type of a supplement (without the persimmon) would contain the following:

monocalcium phosphate
calcium carbonate
magnesium oxide
potassium chloride
calcium pantothenate
choline chloride
folic acid
Vitamin A supplement
Vitamin $D_3$ supplement
Vitamin $B_{12}$ supplement
Vitamin E supplement
Riboflavin
niacinamide
thiamin HCL The amounts of the various components can vary. While Persimmon Pit is shown as one example, other commercial mineral supplement formulations (deer, cattle or the like) could also be modified as well with effective amounts of garlic and sulfur for insect repellancy.

In addition, other minerals or vitamins, e.g., sodium carbonate, selenium, could be added or removed as would be within the skill of the art.

The improved mineral supplement can be made using the conventional techniques used for making solid, powder or liquid supplements. Since these techniques are well know in the art, a further description is not deemed necessary for understanding of the invention.

The mineral supplement is believed to be useful for any ruminant animal, but is particularly attractive for use with deer, and even more so whitetail deer.

Once the mineral supplement is made, it can be placed in one or more locations that are accessible to the ruminant animals. When using it for deer, it is preferred to make the supplement in the form of a lick, and position the lick in a location where deer normally visit, e.g., the wild such as fields, forests, meadows, or the like. In another alternative, the supplement could be positioned in a hole to be accessed by the animals. Of course, it could be used in granular form and put in feeders or the like as well.

If used for other animals such as cattle, it could be provided in these forms or other forms that would be conducive to ingestion by cattle.

Another embodiment of the invention entails using the effective amounts of sulfur and garlic in an animal feed for insect repellency. While a feed may not be desirable when compared to a mineral supplement for attracting animals such as whitetail deer, a feed may be advantageous for other ruminant animals, or may be applicable where it may be desirable to put out feeds for deer, times of drought or the like when natural food sources may be scarce. When employing a feed, it is preferred to use a reduced amount of sulfur and garlic as compared to the amounts noted above for the mineral supplements. The reason for this is that animals consume more feed per day than supplements. For sulfur, a preferred range is believed to be up to around 1.0%, with a more preferred maximum of up to around 0.5%.

The amount of garlic is not as sensitive for animals as the amount of sulfur. Consequently, the same ranges and targets could be used for the feed as for the supplement. From an economic standpoint though, less garlic can be employed in the feed since, as noted above, the animal will consume more feed by weight than supplement. As such, the garlic can range up to only 3.0% rather than 5.0% as with the supplement. The following example shows why the amount of sulfur and garlic can be reduce in a feed. If the animal consumes 1.0 pounds a day of the supplement, this translates to 0.1 pounds of garlic at a 1.0% by weight garlic loading of the supplement. If the animal consume 5 pounds of feed a day, there only needs to be 0.02% by weight of garlic in the feed to ingest the same amount of garlic as the supplement for insect repellency. Similarly, 3.0% sulfur in the supplement can be reduced to 0.6% sulfur in the feed. Of course, these percentages can change depending on the expected consumption of supplement and feed.

It should be understood that an animal feed is different from a feed supplement or a mineral supplement. The Yabiki et al. patent, hereby incorporated by reference in its entirety, particularly its description of garlic powder, exemplifies the difference between feeds and feed additives, and teaches modifying a feed with bile powder, garlic powder, and other feed additives for increasing disease resistance.

The intended animal feed of the invention is one that is distinguished from mineral or feed supplements. Feeds may come in different forms, e.g., roughage, cereals, etc. Roughages mostly likely have a high crude fiber content and low digestible energy content. In contrast, cereals have readily available carbohydrates, sugars, starches, fats and oils, which are more digestible and contain less fiber than roughage-type feeds. With feed, the focus is providing sufficient energy and protein to the animal. In contrast, supplements, whether they are for energy, vitamins, proteins, or minerals, are high in concentration of the material(s) identified as the supplement. Energy supplements can be cereal by-products. Protein supplements, such as soybean or canola meal typically have more than 20% protein. Mineral supplements can concentrate on providing macro minerals such as calcium, phosphorous, sodium, chlorine and potassium, or micro-minerals such as iron, copper, sulfur, zinc, manganese, cobalt, iodine, selenium, molybdenum and chromium.

According to one aspect of the invention, the garlic and sulfur are used in a mineral supplement, particularly for deer. In another aspect, the garlic and sulfur are used in an animal feed, preferably a ruminant animal feed, wherein the primary components are energy and/or protein providers such as hay, alfalfa, grasses, clover, trefoil, haylage, green chop, corn silage, straw, corn stover, corn, wheat, oats, barley, soybeans. These components generally constitute a majority of the feed in terms of weight percent.

The components found in a typical feed composition are as follows: corn chops; soybean meal; dehydrated alfalfa meal, wheat middlings; cane molasses; defluorinated phosphate; calcium carbonate; salt; vitamin A supplement; vitamin d-3 supplement; vitamin E supplement; niacin; choline chloride; D-pantothenic acid; riboflavin supplement, zinc oxide, copper sulfate, zinc sulfate; manganese sulfate; ferrous carbonate; ethylene diamine dihydriodide; magnesium oxide; cobalt carbonate; sodium selenite; and natural and artificial flavorings. It should be understood that this is just one example of an animal feed, and other known feeds can be used as part of the invention. The percentages of the various components may vary, but this variance may occur without altering the basic aspect of the invention.

When using the garlic- and sulfur-containing feed, the feed is fed to the animals using a normal feeding schedule, such feeding resulting in improved repellency to insects, and better animal health.

It should also be understood that when using sulfur in compound form, the sulfur is the major component of the compound. Adding zinc as a desired micro mineral using zinc sulfate would not supply the necessary amount of sulfur for insect repellency.

As noted with the mineral supplements, the animal feed is primarily intended for ruminant animals such as cattle, deer, elk, and the like. However, it is believed that the invention of the combination of effective amounts of garlic and sulfur for insect repellency can have use in feeds for other animals.

As such, an invention has been disclosed in terms of preferred embodiments thereof, which fulfills each and every one of the objects of the present invention as set forth above and provides a new and improved mineral supplement or feed for animals.

Of course, various changes, modifications and alterations from the teachings of the present invention may be contemplated by those skilled in the art without departing from the intended spirit and scope thereof. It is intended that the present invention only be limited by the terms of the appended claims.

What is claimed is:

1. In a mineral supplement for ruminant animals, the improvement comprising the mineral supplement containing an effective amount of garlic and sulfur for insect repellency, wherein salt content is at least 25% by weight basis of the supplement.

2. The mineral supplement of claim 1, wherein the mineral supplement is either solid, liquid, or powder.

3. The mineral supplement of claim 2, wherein the solid is in the form a lick.

4. In a mineral supplement for ruminant animals, the improvement comprising the mineral supplement containing at least 0.1% garlic, 0.5% sulfur, and at least 25% of one or more salts all components based on a weight basis of the total weight of the supplement, the garlic and sulfur being in effective amounts for insect repellency.

5. The supplement of claim 4, wherein the garlic and sulfur amounts are at least 0.5% garlic and 2.0% sulfur on a weight basis of the supplement.

* * * * *